United States Patent [19]

Noetzel

[11] Patent Number: 5,213,774
[45] Date of Patent: May 25, 1993

[54] MOBILE DISINFECTION APPARATUS ESPECIALLY FOR INFECTIOUS WASTE

[75] Inventor: Hans Noetzel, Hanover, Fed. Rep. of Germany

[73] Assignee: Deutsche Babcock Anlagen GmbH, Krefeld, Fed. Rep. of Germany

[21] Appl. No.: 757,475

[22] Filed: Sep. 10, 1991

[30] Foreign Application Priority Data

Sep. 13, 1990 [DE] Fed. Rep. of Germany ... 9013046[U]

[51] Int. Cl.⁵ .......................... B01J 8/04; A61L 2/00; B01B 1/00
[52] U.S. Cl. ..................... 422/292; 422/193; 422/305; 422/309; 588/230
[58] Field of Search .............. 422/292, 305, 309, 193; 588/230

[56] References Cited

U.S. PATENT DOCUMENTS

| | | | |
|---|---|---|---|
| 3,547,577 | 12/1970 | Lovercheck | 422/292 |
| 4,353,874 | 10/1982 | Keller et al. | 422/193 |
| 5,087,418 | 2/1992 | Jacob | 422/23 |
| 5,116,574 | 5/1992 | Pearson | 422/3 |
| 5,122,344 | 6/1992 | Schmoegner | 422/111 |

FOREIGN PATENT DOCUMENTS

| | | |
|---|---|---|
| 0081727 | 6/1983 | European Pat. Off. . |
| 0277507 | 8/1988 | European Pat. Off. . |
| 2505185 | 8/1976 | Fed. Rep. of Germany . |
| 3505570 | 8/1986 | Fed. Rep. of Germany . |
| 3705364 | 5/1988 | Fed. Rep. of Germany . |
| 3800821 | 8/1988 | Fed. Rep. of Germany . |
| 3912751 | 9/1990 | Fed. Rep. of Germany . |

*Primary Examiner*—Jill A. Johnston
*Assistant Examiner*—N. Bhat
*Attorney, Agent, or Firm*—Herbert Dubno

[57] ABSTRACT

A mobile disinfection apparatus for hospital waste has a worm conveyor leading from the bottom of the charging shaft at the back of a trailer bed to the mouth of a rotary tube reactor or rotary kiln enclosed in a heated hood which can be subdivided into separately heated zones. The reactor is formed with scoops which lift the waste comminuted in the charging shaft and cause it to cascade to contact the sterilizing medium and the sterilized waste passes into a discharge housing in which the waste is separated from the sterilizing medium which is recycled. The waste can be discharged and compacted by a worm conveyor which can be swung laterally outwardly from its transport position to discharge the waste for further handling like household or municipal waste.

20 Claims, 4 Drawing Sheets

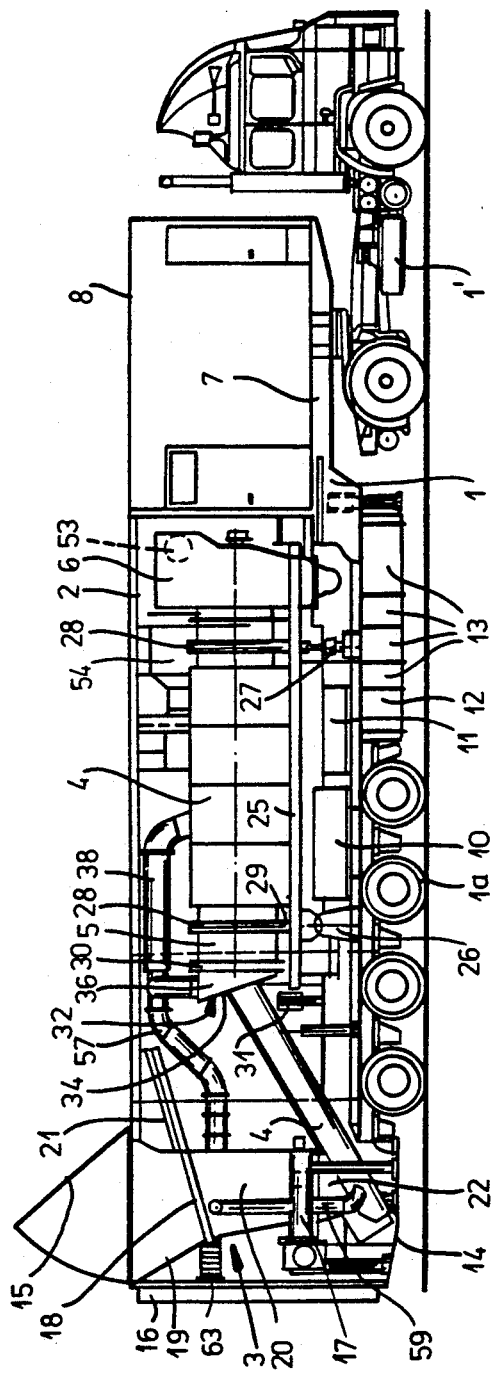
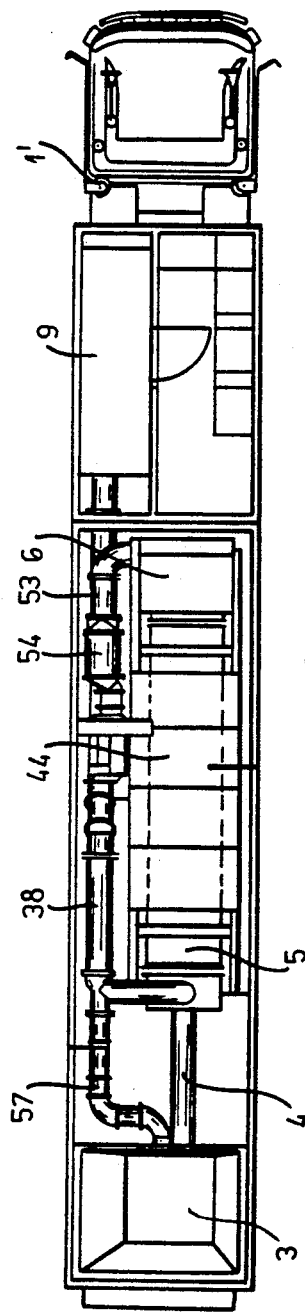
FIG.1
FIG.2

MOBILE DISINFECTION APPARATUS ESPECIALLY FOR INFECTIOUS WASTE

FIELD OF THE INVENTION

My present invention relates to a mobile disinfection apparatus for infectious waste, especially hospital waste and, more particularly, to a mobile disinfection apparatus of the type which comprises a vehicle bed having a chassis or the like upon which a charging shaft with at least one cutting unit and having a gas inlet for sterilizing gas, is mounted, the foot of the shaft communicating with a worm conveyor which carries the comminuted waste out of this shaft.

BACKGROUND OF THE INVENTION

To dispose of infectious waste from hospitals or the like, use has primarily been made heretofore of incinerator installations which may be remote from the hospital and to which the waste may be trucked. The use of open trucks for carrying infectious waste poses a significant problem to people along the path and is barred by regulations or laws for the most part. As a consequence, it has been necessary to provide incinerators on the hospital property which takes up space normally more desirable for other purposes. Some of the incinerators have been in use for decades and can be operated only at high cost and may not be capable of fully decontaminating the infectious waste or may not be sufficiently environmentally sound under present day regulations and statutes.

To minimize the danger to the environment and save costs, it has been proposed to provide disinfection plants in which the hospital waste is so treated that it can be thereafter transported like conventional household waste and treated in a similar manner, e.g. by disposal on a landfill or incineration in a municipal incinerator. It has also been proposed to provide vehicular disinfection plants which can so disinfect the waste that it can be handled like household waste and which can service a number of hospitals.

One system utilizing a vehicular disinfection system in which a charging shaft is provided on a vehicle chassis is described in EP-A2 0 277 507. In this apparatus, the disinfection is effected by heating the shell of the conveyor worm so that the latter forms the disinfection stretch of the path of the waste. A mixture of air and steam is drawn off at the end of the worm conveyor and is passed into the atmosphere after traversing an active carbon filter. The vehicle bed is a trailer of a semi-trailer vehicle in which a tractor is overhung by an end of the trailer.

In the worm conveyor, the material transported thereby is in the form of a loose bulk which is only turned or disturbed to a small extent. Particles within the interior of the bulk material may have little or no intensive contact with the treatment gas (e.g. superheated steam or some other sterilizing medium) and such interior particles tend to be shielded from the heated wall surfaces of the conveyor by the surrounding material.

This drawback is greater, the larger the cross-section of the bulk material movement through the conveyor. A uniform heating of all particles in such a system can only be achieved with very small conveyor cross section and long residence times. This, of course, reduces the throughput. With mobile apparatus, by contrast, the economies of the system require at each pickup location, all of the waste pass through the plant in the shortest possible time and be thoroughly disinfected so that the largest possible number of locations can be serviced by the vehicle.

German Patent 37 05 364 describes another disinfection plant in which the disinfection stretch is also formed by a conveyor worm. This system differs from the first-mentioned system in that the gaseous treatment medium flows in a closed path, i.e. is recirculated and within the conveyor flows in concurrent flow with the waste material to be treated, i.e. in the same flow direction as the waste.

Mention may also be made of German Patent Document DE-OS 25 05 185 from which it is known to disinfect infectious waste continuously utilizing hot air or superheated steam as the disinfection medium in a rotary tube or rotary kiln. Prior to or during this disinfection a comminution is effected and a compactor or press is provided to reduce the volume, at the downstream side of the rotor kiln.

OBJECTS OF THE INVENTION

It is, therefore, the principal object of the present invention to provide a mobile disinfection apparatus which can handle large volumes of infectious hospital waste with high throughput while ensuring uniform intensive heating and thus reliable disinfection.

Another object of the invention is to provide an improved mobile disinfection apparatus which is free from the drawbacks of prior art systems.

SUMMARY OF THE INVENTION

These objects and others which will become more readily apparent hereinafter are attained, in accordance with the present invention, for infectious waste and especially hospital waste, which comprises:

a mobile support bed;

a charging shaft on the bed, the charging shaft having an inlet for infectious waste at an upper portion thereof, an outlet for comminuted waste at a lower portion thereof, comminuting means between the upper and lower portions for comminuting the waste, and means forming a gas inlet communicating with the shaft above the comminuting means;

an upwardly inclined worm conveyor on the bed connected at a lower end with the outlet of the shaft;

an elongated rotary tube reactor on the bed communicating at one end of the rotary tube reactor with an upper end of the worm conveyor for receiving comminuted waste therefrom, the rotary tube reactor being formed internally with lifting scoops raising the comminuted waste in the rotary tube reactor and causing the comminuted waste therein to fall as the rotary tube reactor is rotated and contacting the waste with a sterilizing gas as the waste is caused to move along the reactor toward an opposite end thereof; and a closed discharge housing on the bed at the opposite end of the rotary tube reactor, communicating with the rotary tube reactor to collect sterilized waste therefrom, and formed with a discharge device for discharging sterilized waste collected in the housing and with a suction duct for withdrawing the sterilizing gas from the housing, whereby the sterilizing gas is drawn through said shaft, the conveyor, the rotary tube reactor and the housing.

In the mobile disinfection apparatus of the invention, the disinfection is effected in the rotary tube reactor, i.e.

the rotary kiln, which by comparison to a worm conveyor has a much larger cross section. As a consequence, in a relatively small space occupied by the trailer bed, a high disinfection throughout can be ensured. The rotary action of the kiln with its internal scoops ensures that the comminuted waste which partially fills the section of the rotary kiln or drum can be repeatedly lifted up and cast downwardly so that a trickle curtain of particles is formed within the rotary kiln interior and is intensively contacted with the treatment gas.

The upwardly inclined worm conveyor forms the bridge between the foot of the charging shaft and the inlet opening of the rotary kiln and here serves as an intermediate conveyor. This system, therefore, provides a combination of a charging shaft which can have the full height available for road transport with a rotary kiln whose inlet opening is also relatively high because of the relatively large diameter of the kiln and nevertheless can combine an outlet of the shaft which is close to the road surface with an inlet to the kiln which is well above the road surface.

A preheating is effected in the worm conveyor and the discharge housing can be provided to accommodate a large volume so that it serves as a calming-chamber for the gas stream which is drawn-off to ensure that entrained solids particles, especially the larger particles, will precipitate and settle out of the gas in this chamber.

According to a feature of the invention, the apparatus comprises a shutter plate slidable across the shaft above the comminuting means and subdividing the shaft into a filling chamber above the shutter plate receiving the infectious waste from the inlet of the shaft, and a treatment chamber below the shutter plate and above the comminuting means and feeding the infectious waste to the comminuting means, the means forming the gas inlet communicating with the shaft at the treatment chamber.

Through the use of a sliding plate which serves as a gate between the filling compartment and the pretreating compartment below this plate, the waste to be disinfected can be held in readiness in the filling chamber without danger of escape of infectious particles while the treatment chamber is closed off and can be under the pressure of the disinfection medium without any danger of infectious particles being blown out into the atmosphere.

According to a feature of the invention, the worm conveyor has a conveyor worm formed with a flight pitch progressively upwardly and to the discharge end thereof, thereby effecting a loosening of the material conveyed before it is dumped into the rotary kiln.

According to another feature of the invention the worm conveyor is at its upper end surrounded by a charging housing opening into the rotary tube reactor and formed with an end wall closing the one end of the rotary tube reactor, the end wall having a central passage for delivering the comminuted waste to the rotary tube reactor and a crown of openings surrounding the central passage for admitting sterilizing gas to the rotary tube reactor from said charging housing. The configuration of this end wall thus allows the treating gas steam to be distributed over the entire cross section of the rotary kiln at the inlet thereof, the individual openings lying close to the wall of the rotary kiln or drum so that deposits of the waste along the wall are prevented from interfering with the contact of the waste with the sterilizing gas within the rotary kiln. According to a feature of the invention the charging housing is formed with a distribution chamber partitioned into two branches, a feed pipe communicating with the distribution chamber to supply the sterilizing gas thereto, and a distribution flap being provided at a mouth of the feed pipe opening into the distribution chamber to control flow of the sterilizing gas to the branches. This permits the treatment gas stream to be varied in accordance with its distribution of solids within the rotary kiln, i.e. the trickle curtains formed therein.

According to another feature of the invention, at least one height-adjustment support is provided for the rotary tube reactor enabling adjustment of inclination thereof on the bed. Alternatively or in addition, to control the residence time of the solids in the rotary tube reactor, an adjustable damming device can be provided at the upper end of the rotary tube reactor for controlling the outflow of sterilized waste into the housing.

The temperature can be maintained in the rotary tube reactor by avoiding the radiant heat therefrom by enclosing the rotary tube reactor in a length of a hood to improve temperature control therein. To prevent infectious, contaminated or odoriferous gases from entering, I can provide means formed as a closed circuit for the sterilizing gas including the suction pipe, the feed pipe, a branch pipe connecting the feed pipe with the gas inlet, a blower, and a heater for heating the sterilizing gas.

Advantageously, a bypass duct can be provided to bridge the comminuting means to allow large quantities of gas from the treatment chamber to be fed to the worm conveyor without blockage or restriction by the cutting unit.

Where the vehicle is a trailer of a semi trailer vehicle, the shaft is located at the rear of the trailer and is provided at a rear portion of the shaft with a lifting dumper for dumping infectious waste into the shaft. The trailer can be provided at its rear with a bottom portion extending downwardly below the wheels of the trailer in order to increase the available height for the charging shaft.

The charging device can be an upwardly inclined worm conveyor having a flight pitch decreasing progressively away from the housing, a counterpressure flap, and an outflow pipe connected to a lowest portion of the discharge device. In this manner, the volume of the disinfected waste can be reduced by comparison and its weight also reduced by the pressing of water out of the solid waste. The water is drained by the outflow pipe. The compaction of the material in the worm provides further assurance against escape of the treatment gas.

The discharge device can be mounted so as to be swingable between an inactive position in line with the direction of travel of the vehicle and an operating position in which the discharge device projects laterally.

According to another feature of the invention, a front of the trailer overhanging a tractor is provided in an independent housing with an energy-supply plant including a burner, a steam generator, a heater for the sterilizing gas, a heater for thermo-oil and switching and control units for the apparatus. This allows the limited height above the tractor of the trailer to receive a modular power supply unit. Further assurance against emissions of noxious or toxic materials into the atmosphere can be obtained where the apparatus comprises an enclosure connected with the bed and enclosing the conveyor, the rotary tube reactor and the housing and having a bottom forming a tray. The burner can be connected by an air-suction pipe with the interior of the enclosure or with the filling chamber.

BRIEF DESCRIPTION OF THE DRAWING

The above objects, features and advantages of my invention will become more readily apparent from the following description, reference being made to the accompanying drawing in which:

FIG. 1 is a side-elevational view to scale of a mobile disinfection apparatus according to the invention with the enclosure partly broken away;

FIG. 2 is a plan view of the apparatus of FIG. 1 with the enclosure removed;

SPECIFIC DESCRIPTION

Figure 3:
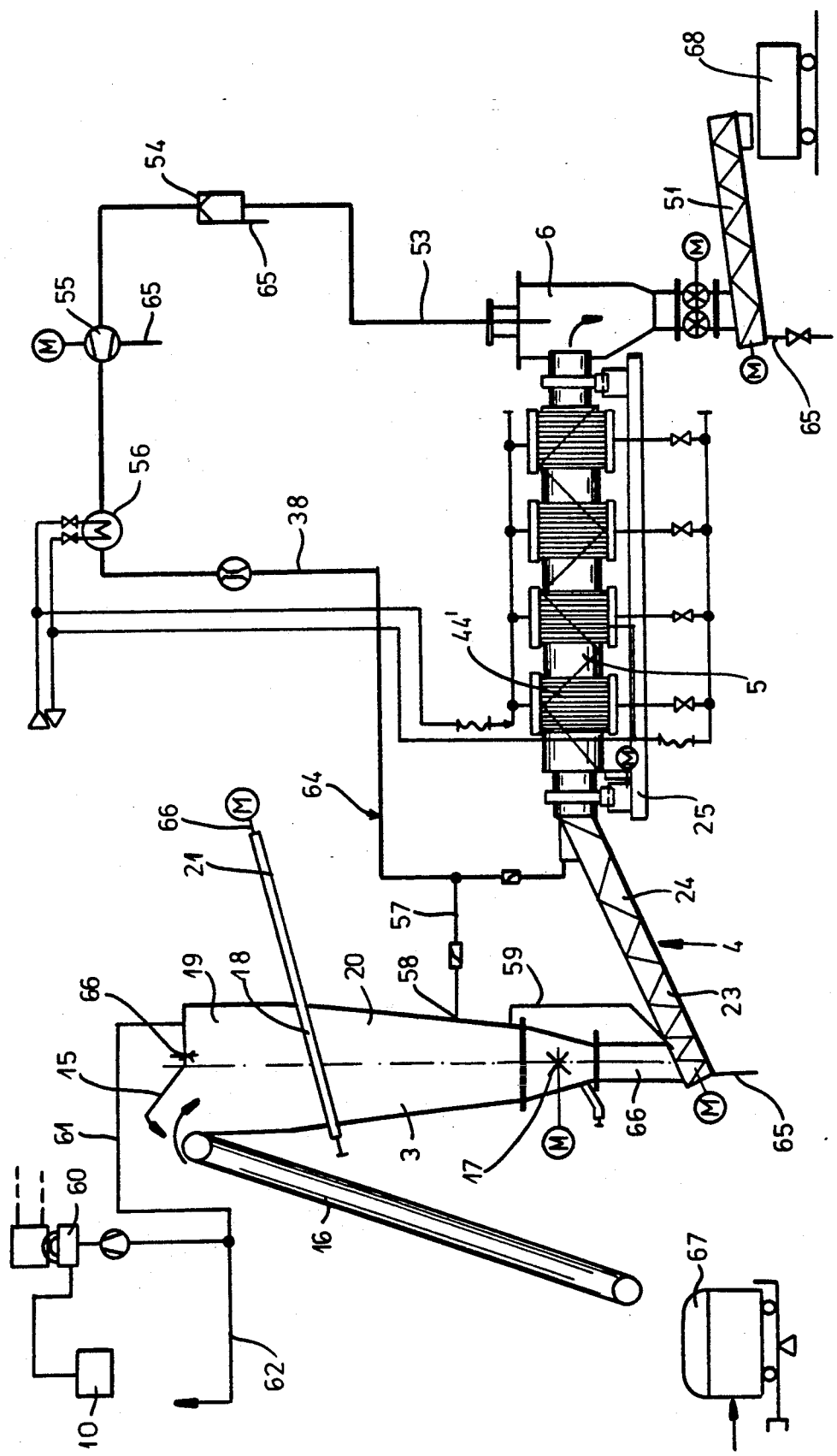
FIG. 3 is a schematic illustration of the parts of the apparatus showing the closed circuit for the disinfected medium.

A trailer 1 of a semi-trailer vehicle having a tractor 1' and overhanging the tractor 1' forms a chassis or bed upon which the remainder of the disinfection plant is mounted. On this tractor, there is found an enclosure or housing 2 whose bottom forms a collection tray for any waste which may fall out of the apparatus, the trailer being dropped at its rear below its wheels 1a to maximize the height available for a charging shaft 3. The housing 2 receives the individual components of the disinfection plant to be described, including the charging shaft 3, a worm conveyor 4, a rotary kiln or rotary tube reactor 5 and a discharge housing 6, all of which are mounted on the bed.

On the neck 7 of the trailer 1 overhanging the tractor 1', in a separate housing 8, a modular energy supply unit 9 is mounted which includes a burner, a steam generator, a heater for the sterilizing or treatment medium, a heat exchanger for thermo-oil and the switching control or service elements for the apparatus. Below the rotary tube reactor 5 on the chassis, are provided the tanks 10 and 11 for fuel oil and thermo-oil.

On the underside of the trailer 1, moreover, a compressor 12 is provided together with receptacles 13 for waste water disinfectant where a liquid disinfectant is used and may be sprayed into the treatment medium or gas stream and fresh water.

The charging shaft 3 which can extend over the full height of the vehicle and narrows downwardly in a funnel-like configuration (see FIG. 3) is mounted on the rear of the trailer 2 above the downwardly extending bottom portion 14 thereof. It can be closed by a flap 15. On the rear side of this charging shaft 3 a lifting and tilting unit 16 is provided for hospital waste containers, one of which has been shown at 67 in FIG. 3, in which the infectious waste is stored and which lifts the infectious waste container and dumps it into the rear end of the charging shaft 3 when the flap thereof is swung upwardly.

At a lower portion of the charging shaft 3 a cutting unit 17 is provided, referred to herein as comminuting means, to chop-up the infectious waste.

The portion of the shaft provided above the cutting unit 17 is subdivided by a slidable plate 18 forming a partition which is inclined downwardly and rearwardly. The partition 18 subdivides the interior of the charging shaft into a filling chamber 19 and a treatment chamber 20. A gas-tight slide casing 21 is affixed on the front side of the charging shaft 3 to receive the slider 18. An actuator 66 is provided on this casing for the slider 18.

Below the cutter 17 a collecting funnel 22 opens at the foot of the charging shaft 3 into the lower end of the worm conveyor 4.

Figure 4:
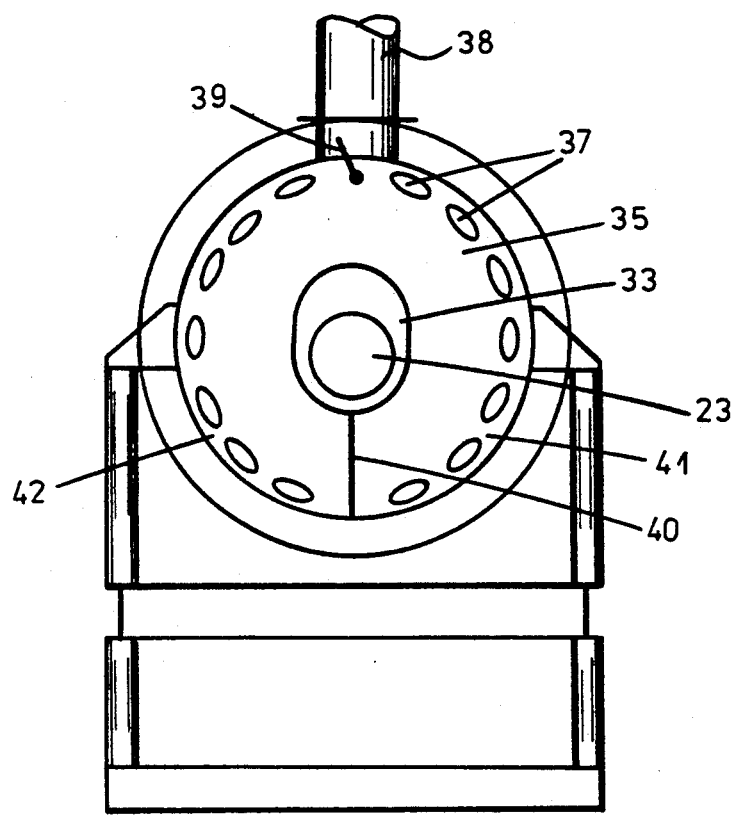
FIG. 4 is an illustration of the charging housing at its connection with the rotary tube reactor.

The worm conveyor 4 comprises a worm 23 the pitch of the flight of which increases in the direction of displacement, i.e. upwardly. The worm is rotatable in an oval worm trough 24 (see also FIG. 4). The worm conveyor 4 is inclined upwardly at about 30° to the horizontal and opens into the rotary tube reactor 5.

The rotary tube reactor 5 is mounted for rotation on a tilting frame 25 pivotally supported at 26 at its inlet side and supported by height-adjustable posts 27 at its discharge side on the chassis of the trailer 1. The rotary tube reactor is rotated by a drive motor 31 whose pinion meshes with a ring gear 30 of the reactor.

Fixed on the tiltable frame 25 is an inlet housing 32 having a passage 33 of oval shape corresponding to the cross section of the worm trough 24 and through which the worm conveyor opens into the rotary tube reactor 5.

At the rear end wall 34 of the inlet housing 32, the worm trough 24 is provided with a compensator not shown in the drawing and allowing relative movement of the inlet housing and the worm conveyor for compensation of thermal expansion and contraction movements. The end wall 34 is inclined (see FIG. 1) so that a downwardly converging wedge-shaped annular distribution chamber 36 is formed between it and an opposite vertical end wall 35. The end wall 35 closes the rotary tube reactor 5 at its inlet side. The end wall 35 is formed with a crown of openings 37 admitting the gaseous treatment medium to the rotary tube reactor along the shell or wall thereof. A central passage 33 in this end wall is traversed by the conveyor as previously noted.

A feed pipe 38 opens into the distribution chamber 36 which is subdivided into two portions by a partition 40 below the passage 33 and opposite the feed pipe 38. A distribution flap 39 at the mouth of this feed pipe can be positioned to distribute the flow primarily to one or the other of the two branches 41 and 42 of the distribution chamber.

The rotary tube reactor is provided internally with angled lifting scoops 43 which can be provided in a plurality of spaced apart crowns along the length of the rotary tube reactor, the scoops of the one crown being angularly offset from the scoops of the neighboring crowns.

The comminuted waste within the rotary tube reactor, as it moves from left to right, is repeatedly lifted by the scoops to cause it to drop in a cascade of particles which intimately contact the sterilizing or treating gas flowing through the reactor.

Figure 5:
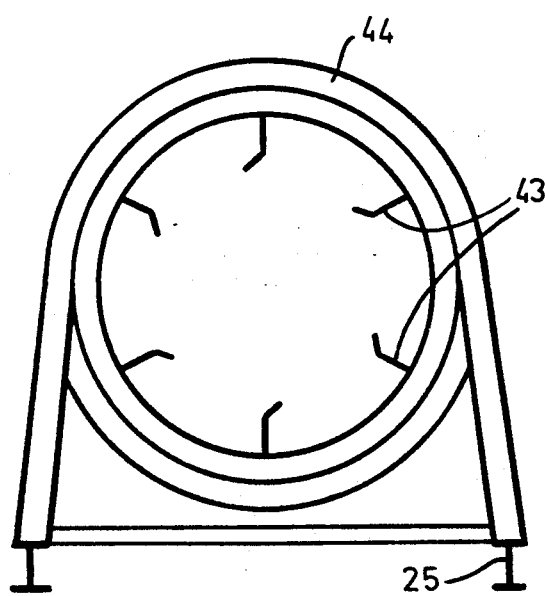
FIG. 5 is a diagrammatic section through the rotary tube reactor.

The rotary tube reactor is enclosed by a hood 44 mounted on the tilting frame 25 and subdivided into four separately heatable zones (compare FIGS. 3 and 5). The rotary tube reactor is enclosed by a hood 44 which has respective groups of radiant heating tubes 44' as shown in FIG. 3, is effected by pumping a heating liquid through these tubes.

The thermo-oil previously described is used for this purpose.

Figure 6:
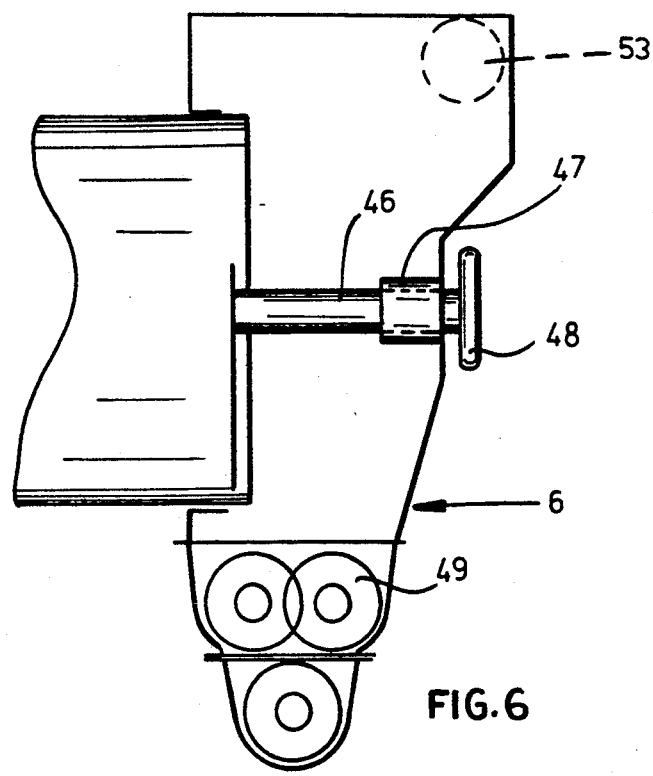
FIG. 6 is a diagrammatic section of the discharge end of the rotary tube reactor and its discharge housing.
Figure 7:
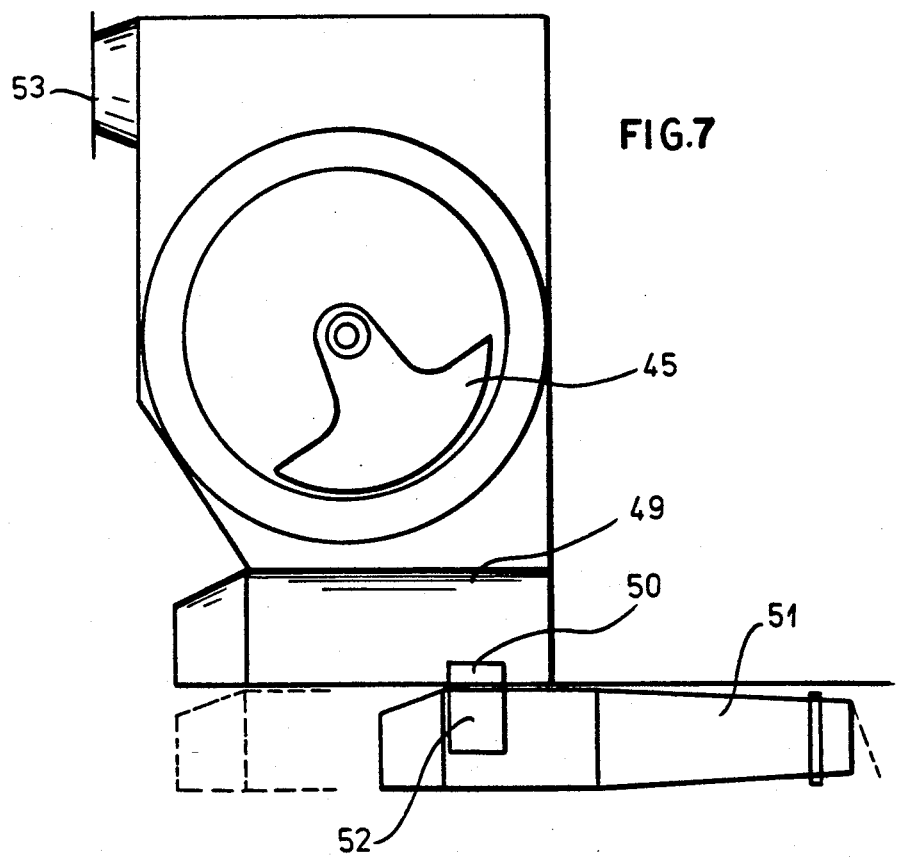
FIG. 7 is an axial view of the latter portion of the rotary tube reactor.

At the outlet end of the rotary tube reactor 5, a damming segment 45 (see FIGS. 6 and 7) is fastened on shaft 46 coaxial with the rotary tube reactor 5. This shaft is journaled at 47 at the front wall of the discharge housing 6 in which the sterile waste accumulates. The shaft 46 together with the damming segment 45 can be angularly adjusted by means represented only diagonally at 48 and arrested in each adjusted position to thereby control the rate at which the waste passes through the rotary tube reactor and hence the residence time of the waste therein.

The discharge housing 6 is fixed to the tilting frame 25. At its lower part, a discharge device is provided which includes a double worm 49 with a discharge opening 50. Below the double worm 49, a worm 51 is provided with decreasing pitch and counterpressure flap. This conveyor can be swung from an inactive transport position shown in FIG. 7 by broken lines, into an operative position in which the conveyor extends laterally. In this position, the feed shaft 52 of the discharge device registers with the discharge opening 50.

The upper portion of the discharge housing 6 forms a widening calming chamber to which a suction pipe or duct 53 is connected and through which the treating medium is withdrawn. The pipe 53 forms part of a closed circuit which also includes (FIG. 3) a fine-dust filter 54, a blower 55 and the feed pipe 38 opening into the distributing chamber 36. The sterilizing gas circulating system also includes a branch pipe 57 which connects the feed pipe 38 with the gas inlet 58 of the treatment chamber 20. From the treatment chamber 20 a bypass pipe 59 opens into the conveyor trough 24 directly at the foot of the shaft 3 to bypass the cutting unit 17.

The burner 60 in the housing 8, shown only schematically in FIG. 3, is provided with an air intake housing to branches 61 and 62, one of which is connected to the feed chamber 19 of the charging shaft 3 while the other opens into the interior of the enclosure 2 so that both the chamber 19 and the enclosure 2 can be under negative pressure. At the rear of the enclosure 2 an intake opening 63 can be provided.

The feed pipe 38 is provided with a fitting 64 so that hot steam can be injected into the feed pipe. At the worm conveyor 4, the discharge worm 51, the filter 54 and the blower 55, at the lowest points of each, discharge pipes 65 can be provided for dirty water and condensate which can be conducted via pipes not shown to the waste water tank. At various locations of the system, ring nozzles 66 can be provided for injecting a disinfectant into the treating gas stream The disinfectant can be an organic disinfectant or hydrogen-peroxide or the like.

The apparatus operates as follows: The infected waste, packed in plastic bags or cartons and stored in a closed container 67 at the hospital, is lifted to the top of the charging shaft 3 by the lifting and tilting unit 1 and held in readiness until a signal indicates that the system is prepared to receive a charge in the filling chamber 19. The flap 15 can only operate after the slider 18 has separated the filling chamber 19 from the treatment chamber 20.

The container 67 is fully emptied into the chamber 19 and the flap 15 is then closed. During the emptying, a negative pressure is generated in the filling chamber 19 by sucking air out via the branch 61 so that emissions into the environment are avoided.

After the flap 15 has been closed, the treatment chamber 20 having emptied, the sliding plate 18 is retracted so that contents of the filling chamber 19 fall into the treatment chamber 20 and into the cutter 17. A multiple air replacement is effected in chamber 19 in that the combustion air for the burner 60 is withdrawn from chamber 19. The plate 18 has meanwhile been returned to its closed position. The comminuted waste passes into the worm conveyor 4 and is loosened while being entrained thereby into the rotary tube reactor 5. The residence time for the comminutable waste in the rotary tube reactor 5 is about 20 minutes and the latter is operated at about 40% filling. The disinfected material, reduced in volume by about 2:1 in the discharge worm 51 can be supplied to a container 68 for disposal as with household waste.

The disinfection is effected in the rotary tube reactor 5 by air and steam forming a treatment medium at a temperature of 140°–160° C. and passing in codirectional flow with the solids. A partial stream of the medium is supplied by the bridge pipe 57 to the treatment chamber 20 and passes with the waste through the cutter 17 and the collecting funnel 22 and partly via the bypass 59 to the worm conveyor 4 and along the latter in concurrent flow to preheat the waste before it enters the rotary tube reactor. A second partial stream is supplied to the feed pipe 38 and via the two branches 41 and 42 and the openings 37 directly to the rotary tube reactor.

In the large-volume discharge housing 6 the treating medium is separated from solids. After residual particles are removed in the fine-dust filter 54 the medium is passed by the blower 55 to the heater 56 where it is again brought to the requisite temperature for sterilization by injection of superheated steam at fitting 64. The optimal steam concentration is provided in this medium.

I claim:

1. A mobile disinfection apparatus for infectious waste, comprising:
   a mobile support bed;
   a charging shaft on said bed, said charging shaft having an inlet for infectious waste at an upper portion thereof, an outlet for comminuted waste at a lower portion thereof, comminuting means between said upper and lower portions for comminuting said waste, and a gas inlet for introducing a sterilizing gas for disinfection communicating with said shaft above said comminuting means;
   an upwardly inclined worm conveyor on said bed connected at a lower end with said outlet of said shaft;
   an elongated rotary tube reactor having an entrance and an exit end opposite one another, the rotary tube reactor being positioned on said bed communicating at said entrance end of said rotary tube reactor with an upper end of said worm conveyor for receiving comminuted waste therefrom, said rotary tube reactor being formed internally with lifting scoops raising said comminuted waste in said rotary tube reactor and causing the comminuted waste therein to fall as said rotary tube reactor is rotated, and a means for contacting said waste with a sterilizing gas as said waste is caused by rotation and by said lifting scoops to move along said reactor toward said exit end thereof; and a closed discharge housing on said bed at said opposite end of said rotary tube reactor, communicating with said rotary tube reactor to collect sterilized waste therefrom, and formed with a discharge device for discharging sterilized waste collected in said housing and with a suction duct for withdrawing the sterilizing gas from said housing, whereby said sterilizing gas is drawn through said shaft, said conveyor, said rotary tube reactor and said housing.

2. The apparatus defined in claim 1, further comprising a shutter plate slidable across said charging shaft above said comminuting means and subdividing said shaft into a filling chamber above said shutter plate receiving said infectious waste from said inlet of said shaft, and a treatment chamber below said shutter plate and above said comminuting means and feeding said infectious waste to said comminuting means, said gas inlet for introducing a sterilizing gas for disinfection communicating with said shaft at said treatment chamber.

3. The apparatus defined in claim 2 wherein said bed is a chassis of a trailer of a semitrailer vehicle.

4. The apparatus defined in claim 3 wherein said shaft is located at the rear of said trailer and is provided at a rear portion of the shaft with a means for lifting and dumping infectious waste into said shaft.

5. The apparatus defined in claim 4 wherein said trailer is provided at said rear with a bottom portion extending downwardly below upper portions of wheels of said trailer.

6. The apparatus defined in claim 3 wherein a front of said trailer overhanging a tractor is provided in an independent housing with an energy-supply plant including a burner, a steam generator, a heater for the sterilizing gas, a heater for thermo-oil and switching and control units for the apparatus.

7. The apparatus defined in claim 6, further comprising an enclosure connected with said bed and enclosing said conveyor, said rotary tube reactor and said housing and having a bottom forming a tray.

8. The apparatus defined in claim 7 wherein said burner is connected by an air-suction pipe with the interior of said enclosure.

9. The apparatus defined in claim 5 wherein said burner is connected by an air-suction pipe with said filling chamber.

10. The apparatus defined in claim 1 wherein said worm conveyor has a conveyor worm formed with a flight pitch progressively increasing upwardly therealong.

11. The apparatus defined in claim 1 wherein said worm conveyor is at its upper end surrounded by a charging housing opening into said rotary tube reactor and formed with an end wall closing said entrance end of said rotary tube reactor, said end wall having a central passage for delivering said comminuted waste to said rotary tube reactor and a crown of openings surrounding said central passage for admitting sterilizing gas to said rotary tube reactor from said charging housing.

12. The apparatus defined in claim 11 wherein said charging housing is formed with a distribution chamber partitioned into two branches, a feed pipe communicating with said distribution chamber to supply said sterilizing gas thereto, and a distribution flap being provided at a mouth of said feed pipe opening into said distribution chamber to control flow of said sterilizing gas to said branches.

13. The apparatus defined in claim 12, further comprising means forming a closed circuit for said sterilizing gas including said suction pipe, said feed pipe, a branch pipe connecting said feed pipe with said gas inlet, a blower, and a heater for heating said sterilizing gas.

14. The apparatus defined in claim 13, further comprising a bypass duct bridging said comminuting means.

15. The apparatus defined in claim 1, further comprising at least one height-adjustable support for positionally adjusting said rotary tube reactor at various angles of inclination relative to said bed.

16. The apparatus defined in claim 1, further comprising an adjustable damming device at said exit end of said rotary tube reactor for controlling outflow of sterilized waste into said housing.

17. The apparatus defined in claim 1, further comprising a heatable hood enclosing said rotary tube reactor and functioning to heat said rotary tube reactor.

18. The apparatus defined in claim 17 wherein said heatable hood is subdivided along the length of said rotary tube reactor into a plurality of zones.

19. The apparatus defined in claim 1 wherein said discharge device is an upwardly inclined worm conveyor with a conveyor worm having a flight pitch decreasing progressively away from said housing, a counterpressure flap, and an outflow pipe connected to a lowest portion of said discharge device.

20. The apparatus defined in claim 19 wherein said discharge device is mounted so as to be swingable between a transport position and an operating position in which said discharge device projects laterally.

* * * * *